United States Patent [19]

Shaw et al.

[11] Patent Number: 5,309,959
[45] Date of Patent: May 10, 1994

[54] DISPENSING APPARATUS

[75] Inventors: Kevin Shaw, Great Sutton; Robert Hardie, Warrington, both of United Kingdom

[73] Assignee: British Nuclear Fuels plc, Warrington, England

[21] Appl. No.: 933,373

[22] Filed: Aug. 24, 1992

[30] Foreign Application Priority Data

Aug. 19, 1992 [GB] United Kingdom ............. 9217616

[51] Int. Cl.$^5$ ................ B65B 43/50; G01N 1/14
[52] U.S. Cl. ................ 141/130; 141/98; 141/103; 422/99; 422/100
[58] Field of Search .......... 141/130, 97, 98, 103, 141/104, 329, 330; 901/8, 16, 31; 422/99, 100, 102

[56] References Cited

U.S. PATENT DOCUMENTS

| | | | |
|---|---|---|---|
| 4,131,426 | 12/1978 | Range | 141/1 |
| 4,854,355 | 8/1989 | Chazot et al. | 141/130 |
| 4,862,932 | 9/1989 | Feinstein et al. | 141/130 |
| 4,869,299 | 9/1989 | Handke | 141/1 |
| 4,922,782 | 5/1990 | Kawai | 901/8 X |
| 5,061,639 | 10/1991 | Lung et al. | |
| 5,067,522 | 11/1991 | Lang et al. | 141/329 |
| 5,102,623 | 4/1992 | Yamamoto et al. | 141/130 X |
| 5,132,088 | 7/1992 | Wakatake | 141/130 X |

FOREIGN PATENT DOCUMENTS

| | | |
|---|---|---|
| 8504157 | 9/1985 | World Int. Prop. O. |
| 9011536 | 10/1990 | World Int. Prop. O. |
| 9011537 | 10/1990 | World Int. Prop. O. |

OTHER PUBLICATIONS

"Robotic system for i.v. antineoplastic drug preparation: Description and preliminary evaluation under simulated conditions," American Journal of Hospital Pharmacy, vol. 46, Nov. 1989, pp. 2286-2293.

Primary Examiner—Ernest G. Cusick
Attorney, Agent, or Firm—William R. Hinds

[57] ABSTRACT

A dispensing apparatus comprises a base, and a robot device on the base having opposing jaw members. A number of stations locate on the base, and cooperate with the robot device in a sequence of operations such as to produce a measured pharmaceutical dose from a supply of a pharmaceutically acceptable substance. One of the stations locates several hypodermic syringes in parallel and a container, and produces relative movement of the appropriate syringe and the container towards and away from each other to arrange that the syringe penetrates and withdraws from the container.

17 Claims, 5 Drawing Sheets

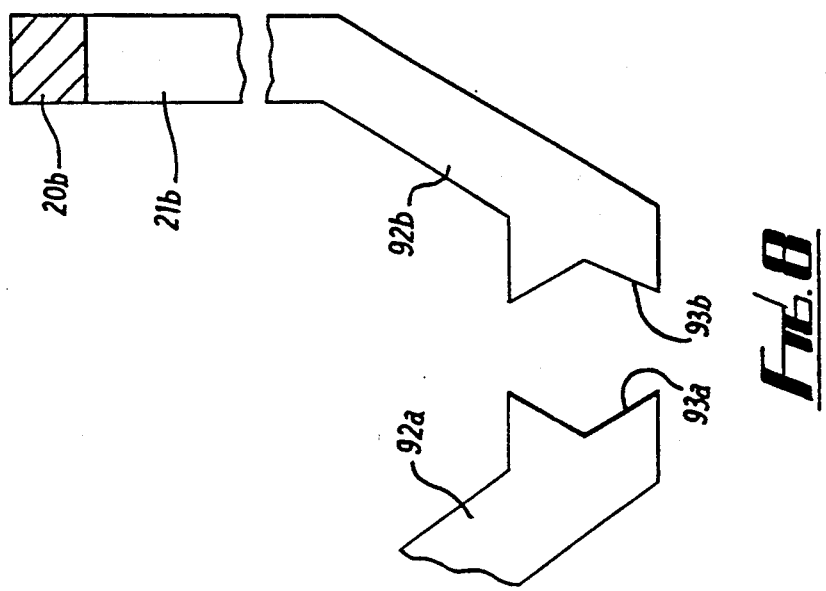
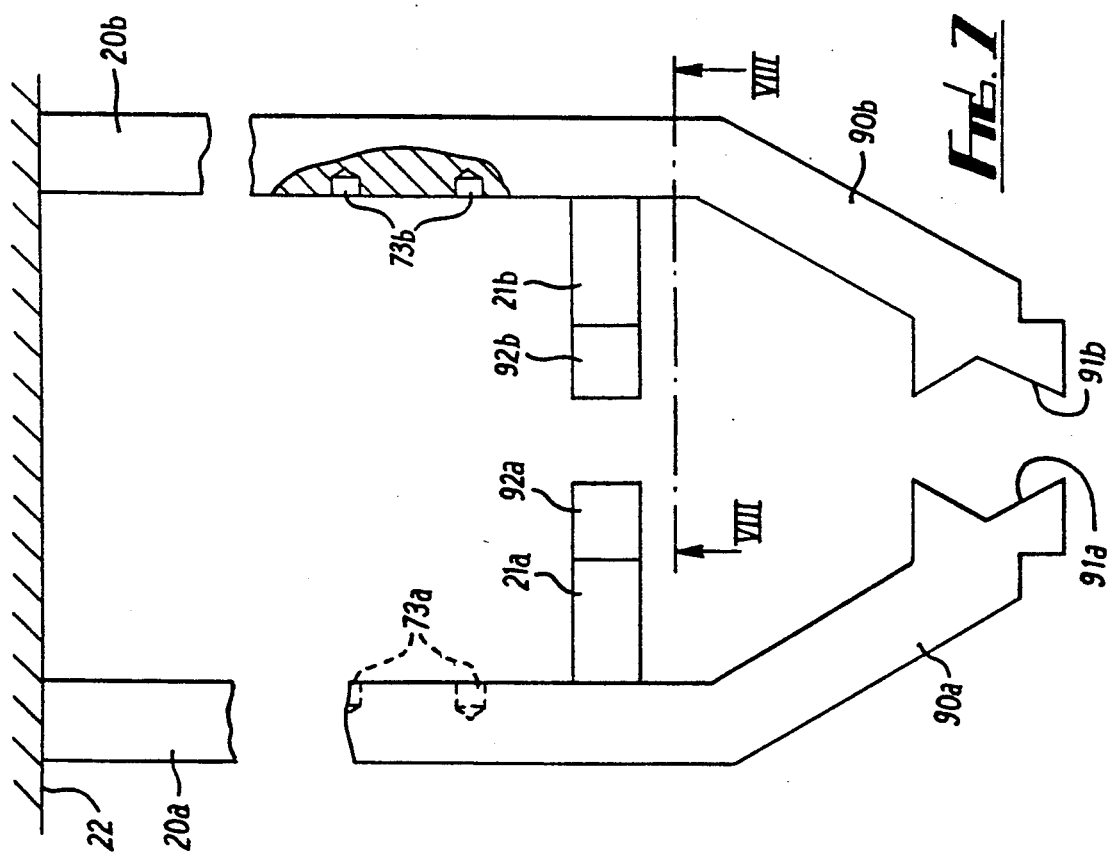

DISPENSING APPARATUS

FIELD OF THE INVENTION

This invention relates to dispensing apparatus for use in the medical field, and more particularly but not exclusively to apparatus for dispensing potentially biologically damaging substances.

In many hospitals large numbers of doses containing potentially biologically damaging substances have to be prepared daily, for example radiopharmaceutical doses. These doses are usually prepared manually in what is an exacting but tedious responsibility for highly skilled staff. It is, therefore, an object of the invention to provide an automated dispenser to simplify the manual operations necessary for preparing doses containing potentially biologically damaging substances whilst maintaining the exacting standards set by medical regulatory bodies.

BACKGROUND AND SUMMARY OF THE INVENTION

According to the present invention there is provided a dispensing apparatus comprising a robot device having gripping means presentable to a plurality of stations, each station being adapted to cooperate with the robot device in a sequence of operations such as to produce a measured pharmaceutical dose from a supply of a pharmaceutically acceptable substance, and one of the stations comprising means for locating in parallel a plurality of medical hypodermic syringes for containing a said substance and for operating a said syringe.

The substance might comprise a potentially biologically damaging substance, such as a radionuclide or a cytotoxin. The measured dose might be retained in a said syringe, or in a medical vial.

Preferably, means are provided for controlling the apparatus in a predetermined sequence of operations.

DESCRIPTION OF THE DRAWINGS

The invention will now be a further described by way of example only with reference to the accompanying drawings in which:

FIG. 7 shows a plan view to an enlarged scale of jaws for the apparatus of FIG. 1;

FIG. 8 shows a view on the line VIII—VIII of FIG. 7;

DESCRIPTION OF THE PREFERRED EMBODIMENTS

Figure 1:
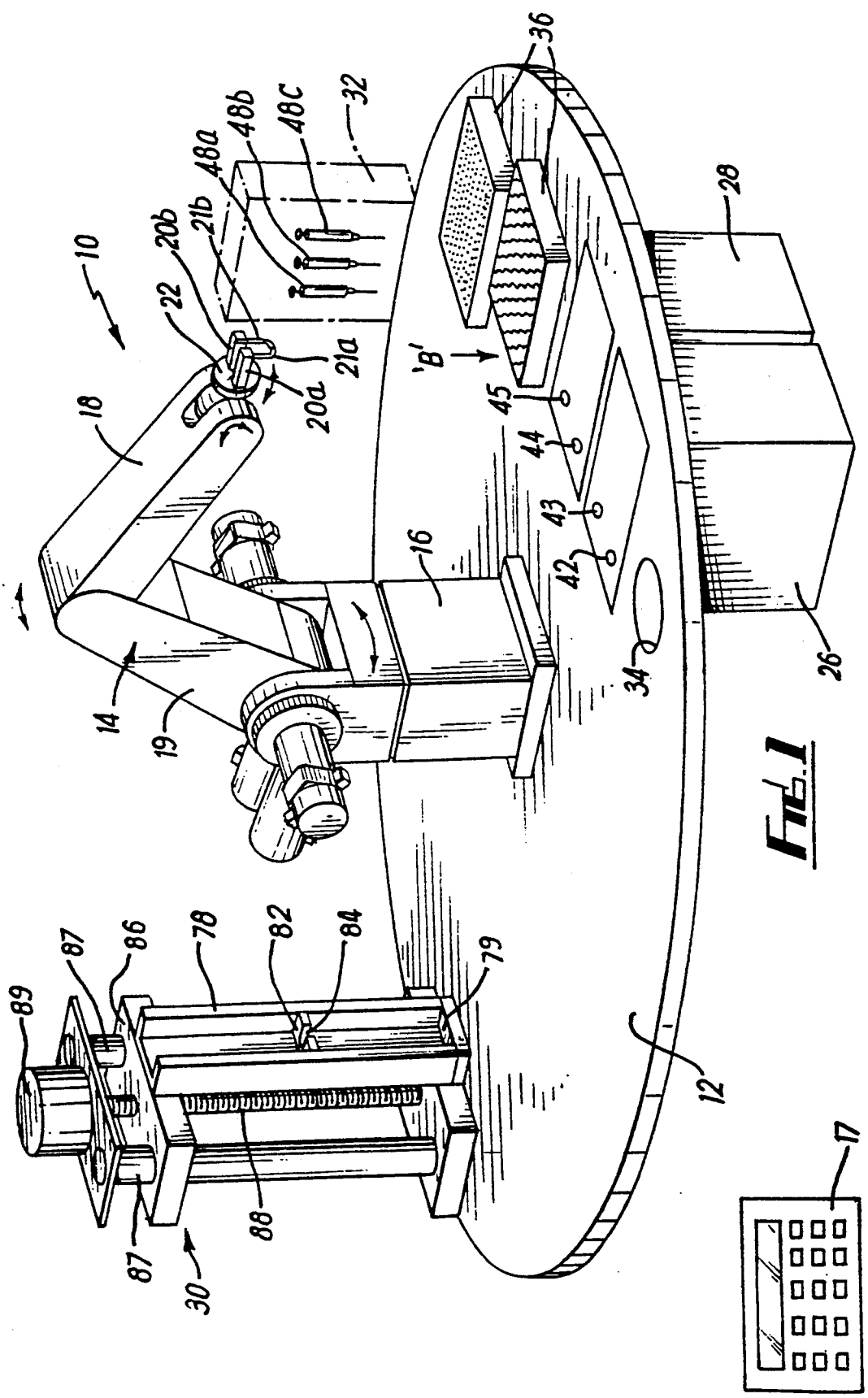
FIG. 1 shows a perspective diagrammatic representation of a dispensing apparatus.
Figure 2:
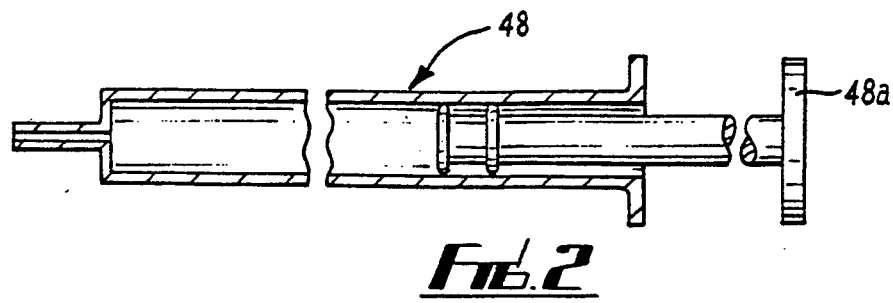
FIGS. 2 to 5 shown in median section a conventional hypodermic syringe and items associated therewith.
Figure 3:
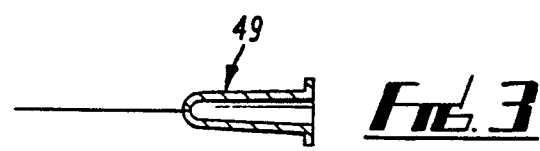
Figure 4:
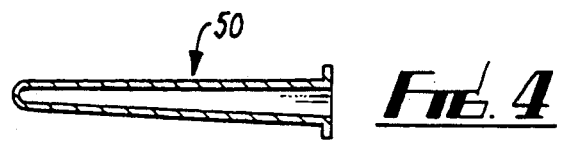
Figure 5:

Referring now to FIG. 1, an automatic dispenser 10 is shown, and comprises a base 12 having thereon an industrial robot device 14 rotatable on a plinth 16 mounted on the base 12 and controlled by a controller 17. The robot device 14 has articulated arms 18, 19, and gripping means in the form of jaw members 20a, 20b having respective depending tangs 21a, 21b at a rotatable wrist element 22 of the arm 18.

The robot device 14 is arranged to present the jaw members 20a, 20b at a number of stations in the form of: radioisotope generators 26, 28 respectively, a monitor assembly 30, a multi-syringe operating assembly 32 (shown only in phantom outline), a waste outlet 34, and trays 36 for holding items to be handled by the dispenser 10.

The generators 26, 28 are proprietary items supplied by companies such as Amersham International, Amersham, United Kingdom, or Dupont, or Mallinkrodt, for the supply of a specific radioisotope, e.g. Technetium 99 m, Thallium, Gallium, or Iodine$^{131}$. Each generator 26, 28 has respective needle-type socket connectors 42, 44, and rotary control valves 43, 45, and usually the generators 26, 28 are arranged so that they supply the radioisotope at different radioactive decay states.

A suitable robot device 14 is that manufactured by: CRS Plus Inc 830 Harrington Court, Burlington, Ontario, Canada L7N 3N4, and distributed in the United Kingdom by: Affordable Automation Ltd, P.O. Box 31, Eccles, Manchester, M30 7QB.

Referring now to FIGS. 2 to 6b various items are shown to be handled by the dispenser 10, namely a hypodermic syringe 48 having a plunger 48a, hypodermic needles 49 for the syringes 48, sheaths 50 for the needles 49, medical hubs 53 for fitting on to the end of the syringes 48 without the needles 49 thereon, and vial shields 54. Each vial shield 54 comprises a pot 56 having a cap 58 secured by a bayonet-type catch 60 to the pot 56, and arranged to contain a conventional medical vial 62.

Figure 6:
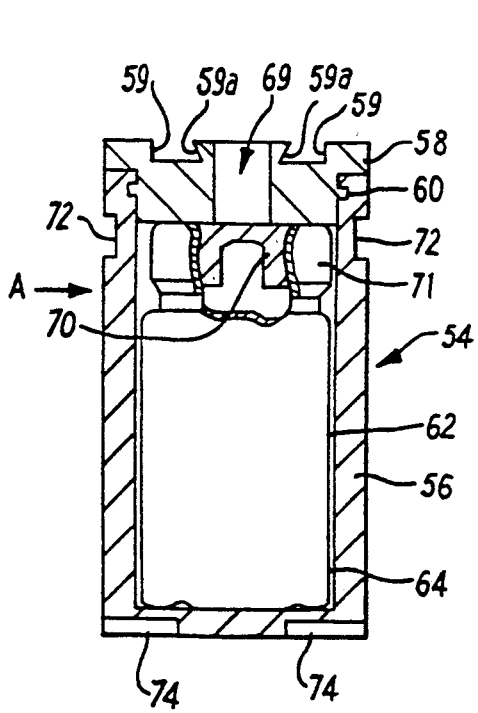
FIG. 6 shows to an enlarged scale a median sectional view of a vial shield containing a medical vial.
Figure 6A:
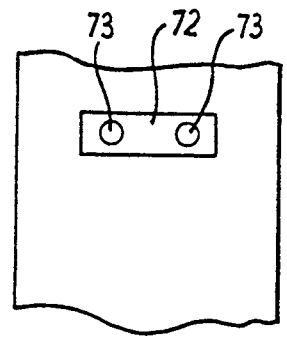
FIG. 6a shows a fragmentary view in the direction of arrow 'A' of FIG. 6.
Figure 6B:
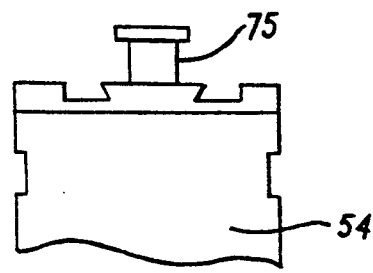
FIG. 6b shows a fragmentary view of a modification to the vial shield of FIG. 6.
Figure 11:
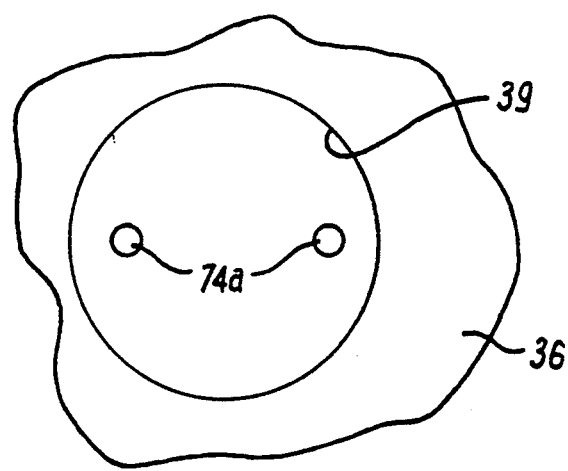
FIG. 11 shows to an enlarged scale a view in the direction of arrow 'B' of FIG. 1.

The cap 58 has parallel grooves 59 with inward wedge-shaped faces 59a which complement the shape of the jaws 20a, 20b. A hole 69 in the cap 58 allows access to a rubber sealing plug 70 retained by a captive metal cap 71 in the vial 62. Two peripheral grooves 72 in the side of the vial shield 54 assist in handling of the vial shields 54 by the jaws 20a, 20b, and two pins 73 in each groove 72 (see FIG. 6a) assist retention of the jaws 20a, 20b. Two slots 74 on a common diameter extend from either side in the base of the vial shield 54 to locate corresponding pins 74a in holes 39 in some of the trays 36 (see FIG. 11). The vial 62 might be an empty bottle, or a bottle containing a powder intended to dissolve in a liquid injected into the bottle, or a bottle containing a medical saline solution. The vial shield 54 is preferably stainless steel, but might be lead with a protective coating. An alternative vial shield 54a (see FIG. 6b) for monitoring for molybdenum is similar to the vial shield 54 except that the hole 69 is omitted and a handle 75 provided.

Referring again to FIG. 1, the monitor assembly 30 comprises a recessed slide 78 having a lower platform 79, and an intermediate support 82 having a slot 84 to locate one of the syringes 48. The slide 78 is joined at its upper end to a table 86 located on guide rods 87, and arranged to be moved vertically by a lead screw 88. The lead screw 88 is operated by a motor 89 so as to lower the slide 78 into a conventional lead shielded, radioactivity detector (not shown) below the table 12.

A preferred form of the jaws 20a, 20b is shown in FIGS. 7 and 8. The jaw members 20a, 20b, have inwardly shaped ends 90a, 90b with opposing V-shaped grip portions 91a, 91b. The depending tangs 21a, 21b have inwardly formed ends 92a, 92b with opposing V-shaped grip portions 93a, 93b. Holes 73a, 73b in the jaws 20a, 20b respectively are arranged to locate the pins 73 of the vial shields 54, 54a, and the outer edges of the grip portions 91a, 91b are arranged to fit into the grooves 59 of the vial shields 54, 54a.

Figure 9:
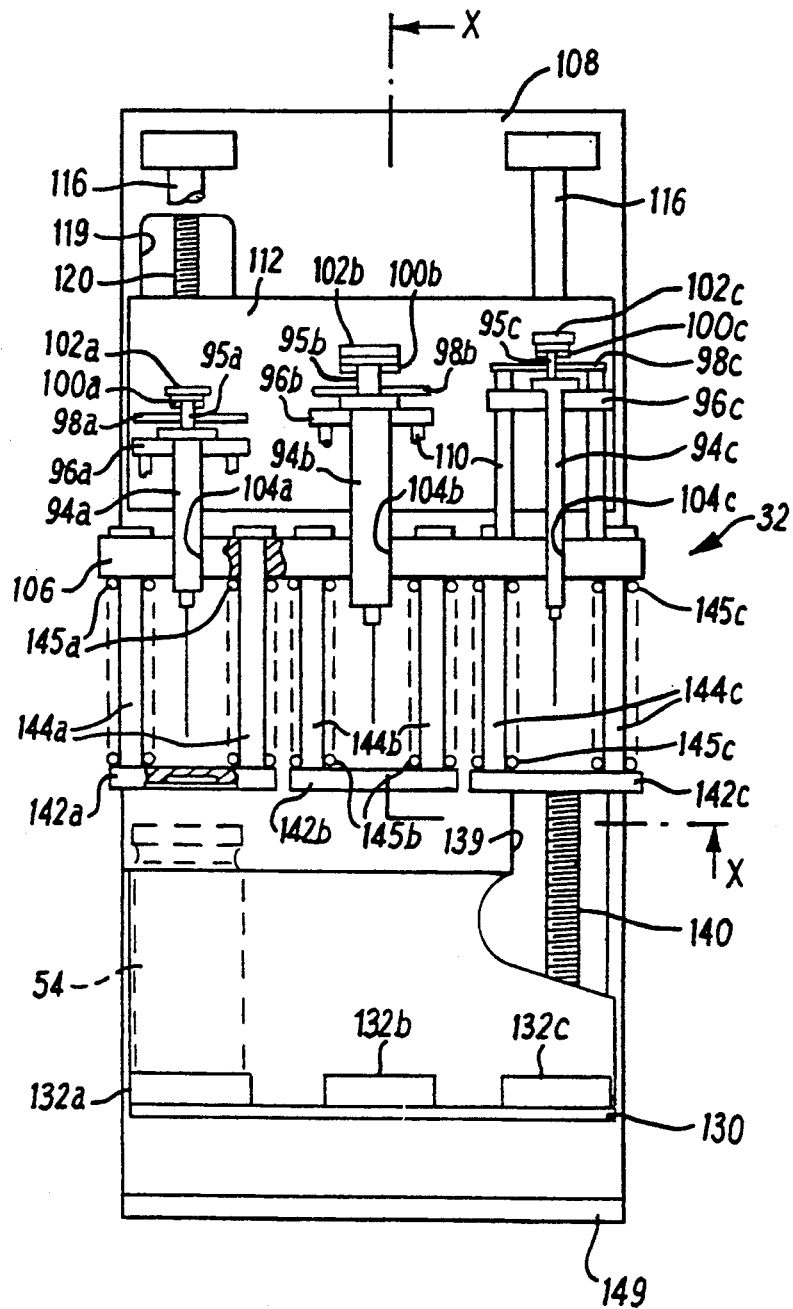
FIG. 9 shows a front view in part section and to an enlarged scale of a syringe operating assembly for the apparatus of FIG. 1.
Figure 10:
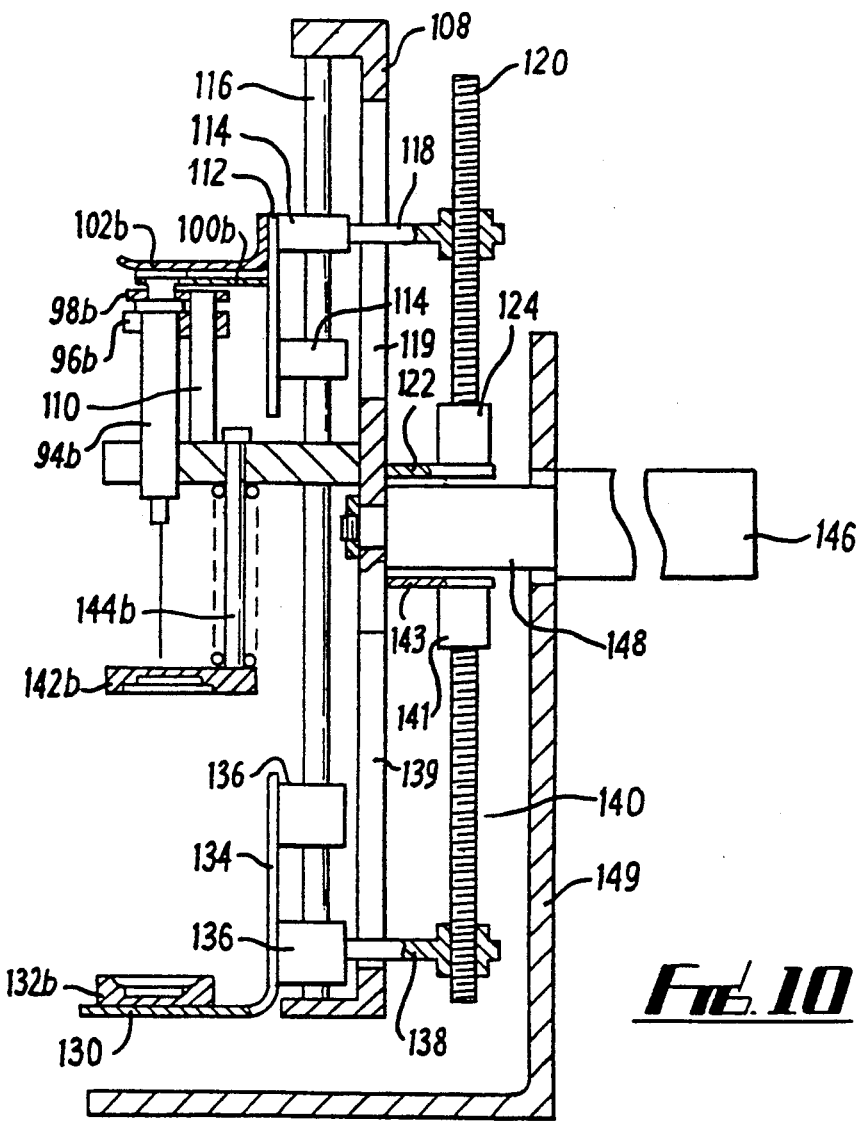
FIG. 10 shows a view on the line X—X of FIG. 9.

A preferred multi-syringe operating assembly 32 is shown in FIGS. 9 and 10 to which reference is made. The assembly 32 is arranged to locate three syringes 94a, 94b, 94c respectively of different capacities on slotted lower shoulders 96a, 96b, 96c where they are retained by slotted upper shoulders 98a, 98b, 98c respectively. Plungers 95a, 95b, 95c of the syringes 94a, 94b, 94c respectively locate on lower slotted tangs 100a, 100b, 100c and are retained by upper tangs 102a, 102b, 102c respectively. The body of the syringes 94a, 94b, 94c extend through respective slots 104a, 104b, 104c in a block 106 secured to an upright wall 108. The lower shoulders 96a, 96b, 96c and the upper shoulders 98a, 98b, 98c are secured to the block 106 through upright support rods 110. The lower tangs 100a, 100b, 100c and the upper tangs 102a, 102b, 102c are supported from one side of an upright plate 112 mounted on linear bearings 114 that slide on two parallel columns 116 supported by the wall 108. An offset arm 118 from an outermost linear bearing 114 extends through an elongate slot 119 in the wall 108, and locates in engagement with a lead screw 120 driven by a motor 124 supported on a bracket 122 from the wall 108 so as to raise and lower the plate 112. A platform 130 has three recessed bases 132a, 132b, 132c respectively to locate vial shields 54 or vials 62, and is shaped to define an upright rear portion 134 mounted by linear bearings 136 on the columns 116. To raise and lower the platform 130, an offset arm 138 extends from an outermost linear bearing 136 through a slot 139 in the wall 108 to engage a lead screw 140 which is separately driven by a motor 141 supported on a bracket 143 from the wall 108. Upper locators 142a, 142b, 142c are supported from the block 106 by sets of slide rods 144a, 144b, 144c respectively. A spigot 148 supported by a stand 149 and rotatable by a motor 146 supports the wall 108 so as to be capable of inverting the all 108.

In use of the dispenser, (e.g. for obtaining a dose of Technetium 99 m) 10, syringes 48, vial shields 54, needles 49, sheaths 50, hubs 53, vials 62, etc. may be stored in the trays 36. The robot device 14 presents an inverted vial shield 54 containing a vial 62 to a selected radioisotope generator 26 or 28. The vial shield 54 is pressed downwards so that the needle of the socket connector 42 or 44 penetrates the hole 69 and the rubber plug 70 of the vial 62. The vial 62 is usually under vacuum so that liquid containing a radionuclide is sucked from the respective generator 26, 28 into the vial 62. The vial shield 54 is then placed by the jaws 20a, 20b in the hole 39 to locate the pins 74a, and the cap 58 is removed. The vial 62 is extracted and placed on the lower platform 79 and lowered by the monitor assembly 30 to the radioactivity detector. The vial 62 is then placed in the vial shield 54a located in one of the holes 38, and the vial shield 54a placed on the lower platform 79 for monitoring by the radioactivity detector. Subsequently the vial 62 is extracted from the vial shield 54a, returned to the original vial shield 54 and placed on the platform 130 (FIGS. 9 and 10). A syringe (e.g. 94a) of the appropriate capacity is fitted into the assembly 32, and the platform 130 is raised so that the needle of the syringe 94a pierces the vial 62 in the vial shield 54. The wall 108 is inverted by the motor 146, and the syringe plunger 95a is lifted and lowered several times by the tangs 100a, 100b so as to withdraw liquid from the vial 62 and expel liquid and air into the vial 62. Finally the plunger 95a is lifted to withdraw liquid from the vial 62 into the syringe 94a. The wall 108 is inverted again, the platform 130 is lowered, and the vial shield 54 removed and placed in one of the trays 36. The syringe 94a, may be removed from the assembly 32, and placed by the robot device 14 into the intermediate support 82 of the monitor assembly 30 so that the radioactivity of the syringe 94a, 94b or 94c may be checked by the detector. A measured dose may be injected into a vial 62 by placing it on the platform 130, raising the platform 130, and lowering the plate 112 so as to depress the plunger 95a, and inject the dose from the syringe 94a into the vial 62.

The wall 108 may be inverted several times to agitate the vial 62. It will be understood that a similar procedure will be followed for a syringe 94b, 94c.

Appropriate fittings (not shown) may be attached to the trays 36 to hold the vial shields 54, or sheaths and enable the robot device 14 to remove and replace the cap 58, etc. Shielded receptacles (not shown) may be located in the trays 36 to locate the loaded syringes 94a, 94b, 94c, vials 62, etc.

Preferred linear bearings are those made by THK Co Ltd, Tokyo 141, Japan, and obtainable inter alia from:

(1) Unimatic Engineering Ltd
122 Granville Road
London NW2 2LN
United Kingdom
(2) THK America Inc
1300 Landmeier Road
Elk Grove Village
Illinois 60007
United States of America It will be understood that if desired the assembly 32 may be modified to accept two, or more than three syringes, and may be operated in an alternative manner from that described above.

If dose dilution is required, saline solution may be withdrawn from an appropriate vial 62 by use of the syringe 48, and then inserted into a required vial 62.

Non-nuclear pharmaceutical doses may be dispensed by the dispenser 10, for example doses containing cytotoxins. The radiopharmaceutical uses of the dispenser 10 may relate to diagnostic and radiotherapeutic applications.

We claim:

1. A dispensing apparatus comprising a base, a robot device on the base, the robot device having gripping means, a plurality of stations at the base, each station being arranged to cooperate with the robot device in a sequence of operations such as to produce a measured pharmaceutical dose from a supply of a pharmaceutically acceptable substance, one of the stations comprising means for locating in parallel a plurality of hypodermic syringes for containing the substance and for operating at least one of the syringes, and said one station including means for locating at least one container relative to said one syringe and for producing relative movement between said one syringe and said at least one container, thereby to arrange for the syringe to penetrate the container and to withdraw from the container.

2. Apparatus as claimed in claim 1, wherein said means for locating in parallel a plurality of syringes locates in parallel syringes of different capacities.

3. Apparatus as claimed in claim 2 wherein each said syringe has shoulders for supporting the syringe, plungers for drawing liquid into and for ejecting liquid from the syringe, and a hypodermic needle, and said one station further comprises:
   a) means for locating the shoulders;
   b) means for locating and for operating the plungers;
   c) means for locating the upper end of the container and for resiliently opposing the relative movement of the container towards the one syringe, and
   d) means for inverting the one station with the one syringe and the container thereon.

4. Apparatus as claimed in claim 1, further comprising a shielded receptacle for receiving the container, a cap for the receptacle, the cap being shaped at an upper end thereof to cooperate with the gripping means.

5. Apparatus as claimed in claim 4, wherein the receptacle has a base with at least one recess therein, and another of the stations having means for locating the receptacle and for engaging in the at least one recess.

6. Apparatus as claimed in claim 4, wherein the cap has a substantially axial hole therethrough for allowing access to the container.

7. Apparatus as claimed in claim 6, wherein the receptacle is shaped at the sides thereof for cooperation with the gripping means.

8. Apparatus as claimed in claim 7, wherein said receptacle is shaped to include pins in the receptacle which cooperate with complementary holes in the gripping means.

9. Apparatus as claimed in claim 6, wherein the receptacle is of stainless steel.

10. Apparatus as claimed in claim 4, wherein the receptacle is of molybedenum.

11. Apparatus as claimed in claim 1, wherein a further said station comprises monitoring means for locating the container or a said syringe, and for moving the container or the said syringe to a radioactivity detector so as to monitor the container or the syringe.

12. Apparatus as claimed in claim 11, wherein the monitoring means is arranged to locate a shielded receptacle for locating the container, the shielded receptacle having a cap shaped at an upper end thereof to cooperate with the gripping means, the shielded receptacle comprising substantially molybdenum, and the monitoring means being arranged to present the receptacle to the radioactivity detector.

13. Apparatus as claimed in claim 3, wherein means are provided for controlling the apparatus in a predetermined sequence of operations.

14. Apparatus as claimed in claim 13, wherein the predetermined sequence includes the inverting means producing a plurality of invertions of the one station so as to agitate the container.

15. Apparatus as claimed in claim 13, wherein the predetermined sequence includes a plurality of operations of the plunger locating and operating means and thereby of the plunger so as to expel air from the syringe.

16. Apparatus as claimed in claim 3, wherein the gripping means comprise opposing first jaw members, and opposing second jaw members projecting from the first jaw members.

17. Apparatus as claimed in claim 16, wherein the robot device includes a wrist element for rotating the gripping means on mutually perpendicular axes.

* * * * *